United States Patent [19]

Orth et al.

[11] Patent Number: 5,324,518
[45] Date of Patent: * Jun. 28, 1994

[54] IMPLANTABLE STRUCTURE FOR CONTAINING SUBSTANCES FOR DELIVERY TO A BODY

[75] Inventors: Jeffrey L. Orth, Salt Lake City; Richard E. Hoffer, Park City; Philip M. Triolo, Salt Lake City, all of Utah

[73] Assignee: Biosynthesis, Inc., Salt Lake City, Utah

[ * ] Notice: The portion of the term of this patent subsequent to Mar. 31, 2009 has been disclaimed.

[21] Appl. No.: 860,434

[22] Filed: Mar. 30, 1992

Related U.S. Application Data

[63] Continuation-in-part of Ser. No. 447,635, Dec. 8, 1989, Pat. No. 5,100,392.

[51] Int. Cl.⁵ .......................... A61K 9/22; A61M 5/32
[52] U.S. Cl. ..................... 424/423; 424/424; 604/93; 604/175; 604/890.1; 604/891.1; 128/899
[58] Field of Search ................. 424/424; 604/93, 175, 604/890.1, 891.1; 128/899

[56] References Cited

U.S. PATENT DOCUMENTS

| | | | |
|---|---|---|---|
| 4,378,016 | 3/1983 | Loeb | 424/424 |
| 4,391,909 | 7/1983 | Lim | 424/424 |
| 4,402,694 | 9/1983 | Ash | 424/424 |
| 4,578,191 | 3/1986 | Jaffrin et al. | 210/323.2 |
| 4,683,200 | 7/1987 | Hirohashi et al. | 424/88 |
| 4,781,714 | 11/1988 | Eckenhoff et al. | 424/424 |
| 4,806,355 | 2/1989 | Goosen et al. | 424/424 |
| 4,892,538 | 1/1990 | Aebischer et al. | 424/424 |
| 4,911,717 | 3/1990 | Gaskill, III | 623/11 |
| 4,936,317 | 6/1990 | MacGregor | 128/784 |
| 4,975,280 | 12/1990 | Schacht et al. | 424/424 |
| 5,084,350 | 1/1992 | Chang et al. | 428/402.2 |
| 5,116,494 | 5/1992 | Chick et al. | 424/424 |

OTHER PUBLICATIONS

Altman, Jean J., et al., "A Bioartificial Pancreas Prevents Chronic Complications of Diabetics in Rats", *Trans Am Soc Artif Intern Organs*, vol. XXXII, 1986, pp. 145–147.

Lacy, Paul E., et al. "Maintenance of Normoglycemia in Diabetic Mice by Subcutaneous Xenografts of Encapsulated Islets", (Washington University School of Medicine, *Reports*, Dec. 20, 1991, pp. 1782–1784.

Lepeintre, J., et al., "Ex Vivo Evaluation in Normal Dogs of Insulin Released by a Bioartificial Pancreas Containing Isolated Rat Islets of Langerhans", *Artificial Organs*, vol. 14., No. 1, Raven Press, Ltd., New York, 1990, pp. 20–27.

Sullivan, Susan J., et al., "Biohybrid Artificial Pancreas: Long-Term Implantation Studies in Diabetic Pancreatectomized Dogs":, *Science*, vol. 252, May 3, 1991, pp. 718–721.

Aebischer, Patrick, et al., "A Bioartificial Parathyroid", *Trans Am Soc Artif Intern Organs*, vol. XXXII, 1986, pp. 134–137.

Aebischer, Patrick, et al., "An Intraperitoneal Receptacel for Macroencapsulated Endocrine Tissue", *Trans Am Soc Artif Intern Organs*, vol. XXXII, 1986, pp. 130–133.

*Primary Examiner*—Thurman K. Page
*Assistant Examiner*—Amy Hulina
*Attorney, Agent, or Firm*—Trask, Britt & Rossa

[57] ABSTRACT

An implantable structure for incorporation into the tissues of a body is provided which retains therein fluid substances or biological substances which produce, or cause to be produced, biochemicals deliverable to the body. The implantable structure is configured to provide insertion and removal of substances therefrom as needed. The implantable structure generally comprises a porous outer member configured to encourage ingrowth of vascularized tissue therethrough, and an inner member of selectively permeable material providing interior space for inserting substances therein and which is structured to prevent ingrowth of tissue therethrough. The inner member is capable of providing immunoisolation to the substances therein as required.

10 Claims, 19 Drawing Sheets

SHEEP 1P
PERCENTAGE OF DELIVERED INSULIN APPEARING PERIPHERALLY

| DATES | AVE DAILY INSULIN DELIVERY McG/DAY | CORRECTED AVE DAILY INSULIN McG/DAY | NORMAL-IZED FLOW | AVE DAILY BLOOD INSULIN McU/M1 | % PERI-PHERAL INSULIN |
|---|---|---|---|---|---|
| 8/14-9/11 | 195 | 195 | 1.00 | 15.33 | .08% |
| 9/11-10/11 | 230 | 192.2 | .84 | 14 | .07% |
| 10/11-11/15 | 195 | 189.2 | .97 | 13.64 | .07% |
| 11/15-12/2 | 226.15 | 212.58 | .94 | 12.67 | .06% |
| 12/12-1/7/91 | 222.31 | 151.17 | .68 | 11.56 | .08% |
| 1/7-2/20 | 482.69 | 376.5 | .78 | 17.73 | .05% |
| 2/20-3/20 | 348.15 | 212.37 | .61 | 14.54 | .07% |
| 3/20-4/23 | 357.19 | 238.67 | .65 | 12.47 | .05% |

Fig. 8

SHEEP 2P
PERCENTAGE OF DELIVERED INSULIN APPEARING PERIPHERALLY

| DATES | AVE DAILY INSULIN DELIVERY McG/DAY | CORRECTED AVE DAILY INSULIN McG/DAY | NORMAL-IZED FLOW | AVE DAILY BLOOD INSULIN McU/M1 | % PERI-PHERAL INSULIN |
|---|---|---|---|---|---|
| 8/15-9/14 | 247 | 247 | 1 | 13.4 | .05% |
| 9/14-10/10 | 230 | 218.5 | .95 | 16.14 | .07% |
| 10/10-11/14 | PROBLEMS WITH DELIVERY - HAND FLUSHED | | | | 0 |
| 11/14-12/14 | 230 | 131.1 | .57 | 14.69 | .11% |
| 12/14-1/8 | 500 | 40 | .08 | 12.98 | .32%* |
| 1/8-2/8 | 437.5 | 345.63 | .79 | 24.4 | .07% |
| 2/8-3/8 | 448.15 | 389.89 | .87 | 26.43 | .07% |
| 3/8-4/20 | 465 | 306.9 | .66 | 31.52 | .10% |

\* ERROR

*Fig. 9*

SHEEP 3P
PERCENTAGE OF DELIVERED INSULIN APPEARING PERIPHERALLY

| DATES | AVE DAILY INSULIN DELIVERY McG/DAY | CORRECTED AVE DAILY INSULIN McG/DAY | NORMALIZED FLOW | AVE DAILY BLOOD INSULIN McU/M1 | % PERIPHERAL INSULIN |
|---|---|---|---|---|---|
| 9/5-10/3 | 195 | 214.5 | 1.10 | 11.67 | .05% |
| 10/3-11/2 | 195 | 198.9 | 1.02 | 13.89 | .07% |
| 11/2-11/28 | 207.86 | 218.25 | 1.05 | 11.75 | .05% |
| 11/28-1/2/91 | 207.71 | 159.94 | .77 | 12.20 | .08% |
| 1/2-2/6 | 338.32 | 335.44 | .99 | 13.81 | .04% |
| 2/6-3/6 | 351.85 | 232.22 | .66 | 12.37 | .05% |
| 3/6-4/23 | 356.38 | 163.94 | .46 | 15 | .09% |

Fig. 10

SHEEP 4P
PERCENTAGE OF DELIVERED INSULIN APPEARING PERIPHERALLY

| DATES | AVE DAILY INSULIN DELIVERY McG/DAY | CORRECTED AVE DAILY INSULIN McG/DAY | NORMALIZED FLOW | AVE DAILY BLOOD INSULIN McU/M1 | % PERIPHERAL INSULIN |
|---|---|---|---|---|---|
| 9/7- 10/5 | 195 | 296.4 | 1.52 | 15.8 | .05% |
| 10/5- 10/31 | 230 | 230 | 1 | 14.43 | .06% |
| 10/31- 11/27 | 230 | 151.8 | .66 | 16.7 | .11% |
| 11/27- 1/4/91 | 210.9 | 271.58 | 1.01 | 12.21 | .04% |
| 1/4- 2/22 | 318.37 | 245.14 | .77 | 10.82 | .04% |
| 2/22- 3/27 | 356.25 | 217.31 | .61 | 14.98 | .07% |
| 3/27- 4/21 | 328.85 | 200.6 | .61 | 14.95 | .07% |

Fig. 11

SHEEP 1P
TIME TO APPEARANCE AND PEAK VALUES OF INSULIN AFTER PUMP BOLUS

| DAYS POST IMPLANT | PEAK MINS FROM BOLUS | PEAK VALUE McU/M1 | 1ST APPEARANCE MINUTES | VALUE McU/M1 |
|---|---|---|---|---|
| 80 | 30 | 90 | 15 | 55 |
| 106 | 30 | 155 | 15 | 112 |
| 141 | 30 | 127.9 | 15 | 100.6 |
| 176 | 30-60 | 134 | 15 | 118.6 |
| 204 | 30 | 15.75 | 15 | 15.25 |
| 218 | 30 | 28.6 | 30 | 28.6 |
| 232 | 60 | 41.6 | 15 | 33.1 |

*Fig. 12*

SHEEP 2P
TIME TO APPEARANCE AND PEAK VALUES OF INSULIN AFTER PUMP BOLUS

| DAYS POST IMPLANT | PEAK MINS FROM BOLUS | PEAK VALUE McU/M1 | 1ST APPEARANCE MINUTES | VALUE McU/M1 |
|---|---|---|---|---|
| 77 | NONE | 21 | VALUE DID NOT INCREASE | |
| 104 | NONE | 10 | VALUE DID NOT INCREASE | |
| 142 | NONE | 16 | VALUE DID NOT INCREASE | |
| 177 | 60... | 70.9 | 15 | 31.9 |
| 191 | 60-90 | 68 | 15 | 37.6 |
| 205 | 30... | 64 | 15 | 32 |
| 224 | 30-60 | 85 | 15 | 80.3 |
| 231 | 30... | 98.2 | 15 | 55 |

...PUMP BOLUS WAS FOLLOWED BY PDP BOLUSES SO THE INSULIN VALUE CONTINUED TO RISE.

*Fig. 13*

SHEEP 3P
TIME TO APPEARANCE AND PEAK VALUES OF INSULIN AFTER PUMP BOLUS

| DAYS POST IMPLANT | PEAK MINS FROM BOLUS | PEAK VALUE McU/M1 | 1ST APPEARANCE MINUTES | VALUE McU/M1 |
|---|---|---|---|---|
| 92 | 60 | 114 | 15 | 65 |
| 119 | 30 | 165 | 15 | 152 |
| 145 | 15 | 71.1 | 15 | 71.1 |
| 189 | 60 | 6.94 | 30 | 6.25 |
| 217 | 30-60 | 31.38 | 30 | 31.38 |
| 231 | 30-60 | 26.5 | 30 | 19.13 |

Fig. 14

SHEEP 4P
TIME TO APPEARANCE AND PEAK VALUES OF INSULIN AFTER PUMP BOLUS

| DAYS POST IMPLANT | PEAK MINS FROM BOLUS | PEAK VALUE McU/M1 | 1ST APPEARANCE MINUTES | VALUE McU/M1 |
|---|---|---|---|---|
| 90 | 150 | 23 | 90 | 13 |
| 120 | 15 | 67.63 | 15 | 67.6 |
| 145 | 15 | 12.5 | 15 | 12.5 |
| 176 | 30 | 36.75 | RESPONSE TO FLUSH | |
| 204 | 15 | 227.88 | RESPONSE TO FLUSH | |
| 223 | 15 | 24.38 | 15 | 24.38 |
| 232 | DID NOT INCREASE FROM 0 VALUE | | | |

*Fig. 15*

IMPLANTABLE STRUCTURE FOR CONTAINING SUBSTANCES FOR DELIVERY TO A BODY

BACKGROUND

Related Applications: This application is a continuation-in-part of the commonly assigned application bearing Ser. No. 07/447,635, filed Dec. 8, 1989, now U.S. Pat. No. 5,100,392, issued Mar. 31, 1992, the contents of which are incorporated herein by reference.

FIELD OF THE INVENTION

This invention relates generally to devices for implantation in a body for delivery of chemical substances thereto. Specifically, this invention relates to implantable devices which are structured to be incorporated into the tissue of the body into which it is implanted, and which are structured to contain biological substances or matter therein for providing a biochemical to the body, or for stimulating production of a chemical substance by the body.

STATE OF THE ART

Significant efforts have been expended in the past decade to develop means for dealing with certain chemical deficiencies or imbalances in the body. In particular, efforts have been directed to alleviating insulin deficiency in diabetic patients. Similar research has also been conducted with respect to delivering hormones, pain killers and the like to a body. In an attempt to eliminate the need for daily subcutaneous injections of drugs, researchers have developed implantable devices which are designed to deliver a discrete dosage of a chemical to the body, usually activated by an external source such as a pump.

Implantable devices have generally been useful for delivering a dosage of chemical to a patient, but some difficulty has been encountered in regulating the dosage of chemical delivered to the body. For example, insulin must be provided to a diabetic patient in response to increased blood glucose. It is often difficult to estimate what level glucose is extant in the blood, and implantable devices have not yet been adapted for use with glucose sensing devices. Typically, therefore, a single dosage of insulin is provided to the patient with an initial high level of insulin and a later levelling off of insulin in the blood.

The problems encountered with regulating drug delivery have led, in more-recent years, to development of implantable systems and devices which encapsulate those tissues or cells which are responsible for producing chemical substances needed by the body. Because such tissue or cells typically come from a donor, which may or may not be the same species, research has been directed to developing an implantable system which provides an immunoprotective barrier between the body and the implanted tissue or cells. For example, islet cells which are responsible for production of insulin have been enclosed in semipermeable membranes which allow only glucose and insulin to pass therethrough, thereby providing an immunosuppressant condition around the cells.

Examples of systems which encapsulate cellular or tissue material in semipermeable gelatinous membranes are disclosed in U.S. Pat. No. 5,084,350 to Chang, et al., issued Jan. 28, 1992, disclosing a method for encapsulating biologically active material in association with gelled beads contained within a semipermeable capsule; U.S. Pat. No. 4,806,355 to Goosen, et al. issued Feb. 21, 1989, disclosing microencapsulation of living cells in a semipermeable membrane of hydrogelatinous material; and U.S. Pat. No. 4,391,909 to Lim issued Jul. 5, 1983, disclosing encapsulation of islet or liver cells in spheroidal semipermeable membranes comprising a polysaccharide with acidic groups cross-linked with a polymer.

Examples of structures developed to contain fluid or cellular substances are disclosed in U.S. Pat. No. 4,378,106 to Loeb issued Mar. 29, 1983, which discloses a device having an extracorporeal portion and a semipermeable subcutaneous portion into which cells or other material are inserted through a replaceable sack; U.S. Pat. No. 4,578,191 to Jaffrin, et al., issued Mar. 25, 1986, discloses a U-shaped tube of material the configuration of which provides movement of blood thereabout to promote intercommunication of glucose and insulin to the cells; U.S. Pat. No. 4,911,717 to Gaskill issued Mar. 27, 1990 discloses a semipermeable catheter system for intravascular implantation into which cells can be placed and removed; and Sullivan, et al., "Biohybrid Artificial Pancreas: Long-term Implantation Studies in Diabetic, Pancreatectomized Dogs" *Science* Vol. 252 (May 3, 1991), which describes a tubular spiralled membrane formed within a housing containing islet cells, the tubular membrane being interconnected between an artery and a vein for transport of blood therethrough.

Various problems have been encountered with the aforementioned systems due to deficiencies in design and due to the inherent death of cellular material over time. Specifically, cellular material encapsulated in gel-like membranes are generally free to migrate in the body following implantation, and once spent, the cells are not retrievable for replacement. Thus, new encapsulated membranes must be implanted with the attendant risk of inflammation and infection at the injection site. Further, the membranes may rupture thereby exposing xenogeneic cells to the body.

Prior art implantable devices have also proven to be troublesome for various reasons including, non-retrievability of the cellular material after implantation and death of the cells, movement of the device within the body causing inflammatory response and fibrotic encapsulation of the device, and obstruction or clotting, particularly observed when the device is implanted intravascularly. Necrosis of vascular grafts have been observed with devices interconnected between blood vessels in the body. Prior art pancreatic devices have also been inefficient or incapable of producing the desired delivery of insulin to the body due to poor insulin/glucose diffusion kinetics.

Thus, it would be an improvement in the art to provide an implantable, incorporable device structured to retain biological material therein for producing or causing the production of biochemicals for delivery to the body, which is structured to provide immunoisolation of such biological material, and which provides for replacement or supplementation of material within the device.

SUMMARY OF THE INVENTION

In accordance with the present invention, implantable structure for incorporation into the tissues of a body is provided which retains therein fluid substances or biological substances which produce, or cause to be produced, biochemicals deliverable to the body. The implantable structure is configured to provide insertion and removal of substances therefrom as needed. While the implantable device may be used to implant many different types of sub-stances in the body, the disclosure focuses on use of the device with insulin and pancreatic islet cells for production of insulin, as an example.

The implantable structure generally comprises a porous outer member configured to encourage ingrowth of tissue therethrough, and an inner member of selectively permeable material providing interior space for inserting substances therein and which is structured to prevent ingrowth of tissue therethrough. The inner member is capable of providing immunoisolation to the biological substances therein as required. The implantable structure further comprises at least one port means communicating with the interior space of the inner member for insertion and removal of substances therefrom.

The outer member of the implantable structure may be suitably formed from a porous synthetic material having irregularly shaped pores forming tortuous pathways through the thickness of the material. A predominant number of the pores are "open-celled," meaning that there is a first opening associated with a first surface of the material and a second opening associated with a second surface of the material. A number of the pores are "close-celled," meaning that there is only a single opening into the pore from any surface. Many of the pores, both open-celled and close-celled, are interconnected as a result of the tortuous and irregular shape of the pores.

The pore size of the outer member is selected to provide ingrowth of tissue through the pores while retaining adequate vascularization. The pore size may therefore range from about 60 microns to about 500 microns, with a preferred pore size ranging from about 160 to about 300 microns. Pore sizes in this range allow vascularized connective tissue to grow into and through the pores of the material from the surrounding environment in which the implantable structure is placed. Pore sizes in this range also prevent unregulated growth of tissue which eventually leads to encapsulation of the device by fibrotic tissue.

The outer member is configured to prevent an inflammatory response with the surrounding tissue. That is, the outer member is constructed to be non-reactive with the surrounding tissue so that ingrowth may occur and irritation of the tissue is avoided. It is irritation of the surrounding tissue, usually from movement of a device or structure, which causes an inflammatory response in tissue thereby forming scar tissue. Encapsulation of a structure with scar tissue leads to occlusion and clogging of the device with resulting loss of function. The present structure presents an advantageous means of preventing the formation of scar tissue, and thus encapsulation, by encouraging regulated ingrowth of vascularized tissue into the device. Ingrown tissue stabilizes the implant and incorporates it into the surrounding tissue environment thereby preventing overt movement of the device.

The advantages of an incorporable device vis á vis a non-incorporable device are described in U.S. Pat. No. 5,100,392. Specifically, promoting the ingrowth of vascularized tissue into the device provides stability and permanence. Because the device becomes incorporated into the patient's body tissue, the device cannot move and no inflammation or infection occurs. Further, the ingrowth of tissue provides an intimate association between the tissue of the body and the substances retained within the device. Therefore diffusion kinetics are improved over non-incorporable devices.

The inner member is formed of a selectively permeable synthetic material, the pores of which are sized to permit only smaller molecules to pass therethrough. The pores are not large enough to allow ingrowth of tissue. The pore size of the inner member material may be from about 30,000 Daltons to about 25 microns. Therefore, the pore size may be selected to permit passage of only smaller molecules such as glucose and insulin therethrough, but is selected to be impervious to macrophages and other structures which are primarily responsible for immunoreactive events. A particularly suitable material for formation of the inner member may be polysulfone or polyethylene.

The inner member is positioned within the outer member. The inner member is structured to provide an interior space into which substances may be placed. At least one port means is associated with the implantable structure to provide communication of substances through the outer member and inner member to the interior space. Conduit means may typically be associated with the port means to provide communication of biological substances from a source external to the implantable structure to the interior space. A particularly suitable embodiment includes at least two port means, and conduits associated with each, for providing an inlet and an outlet relative to the interior space.

In a first embodiment, the implantable structure is configured to provide a single inner member formed within an outer member, and a single interior space is provided within the inner member. The inner member may be formed with two open ends, one of which is associated with the port means for introduction of biological substances therein. The other end is open to the environment upon initial implantation. In this embodiment, termed for convenience as a "flow-through" device, vascularized tissue grows into the porous outer member until it reaches the selectively permeable inner member where tissue ingrowth ceases. The open end of the flow-through device may become over-grown with connective tissue from the surrounding environment to effectively close off the end of the device.

The flow-through configuration provides a permanently incorporated catheter for delivery of fluid substances to the patient. When the open end of the device remains unobstructed with tissue, fluid substances injected into the device may simply flow through the device and into the surrounding tissue. If the open end becomes overgrown with tissue, the tissue forms a sort of diaphragm which is distendible to some extent. The tissue diaphragm may thus provide variable pressure within the device to urge diffusion of the fluid substance through the inner member and the vascularized tissue in the outer member. It is notable that vascularized tissue will generally not grow into the open end of the device given the size of the opening coupled with the effects of constant injection of fluid through the device.

Fluid substances, such as insulin or other drugs, are introduced into the interior space via the port means and associated conduit. Where, for example, insulin is injected into the device, insulin may be diffused through the wall of the inner member and into the surrounding ingrown vascularized tissue. Insulin is diffused through the ingrown tissue in response to increased glucose levels existing in the vascularized tissue. A glucose sensor may also be associated with the implantable structure to sense rising levels of glucose and to activate an infusion pump.

In an alternative embodiment, the implantable structure is configured with an inlet port and an outlet port, both of which communicate with the interior space formed in the inner member. Thus, biological substances can be introduced to the interior space through the inlet port, and the interior space may be flushed of its contents through the outlet port. Thereafter, new biological substances can be introduced into the interior space.

In any given embodiment, the implantable structure provides means for introducing biological substances into the interior space and means for removing biological substances therefrom. For example, islet cells may be introduced into the device through a port means and the cells may remain in place for several months. When the cells have ceased to function, or need supplementation with new cells, the old cells may be flushed out through the port means and new cells may be introduced into the device. The ability to remove or replace biological substances within the implantable structure without having to remove the structure itself, or without causing trauma to the device or to the patient through manipulation within the body, provides a significant advantage over prior art devices.

The double lumen configuration (that is, an outer member and an inner member disposed therein) of the implantable structure provides an immunobarrier between the host tissue and the biological substances introduced into the device, while providing an immediate interface between the host tissue and the implanted biological substance. Because of the intimate association of host tissue and biological substance, improved glucose/insulin kinetics are observed.

The types of biological substances which may be introduced into the implantable structure are numerous and are determined by the kind of therapy required. For example, a biochemical may be introduced directly into the structure for administration to the body. Such biochemicals may include insulin, human growth factor, analgesics, hormones, or the like. Other biological substances which may be implanted include xenogeneic tissues or cellular material which is harvested, cloned or otherwise derived from another animal or species. Such xenogeneic tissue may be capable of producing a biochemical needed by the host animal or may be capable of triggering a particularly desired result in the host animal. Other materials which may be introduced into the device include monoclonal antibodies or viruses, such as the HIV virus, which may be used to stimulate the natural disease fighting defenses of the host animal.

BRIEF DESCRIPTION OF THE ILLUSTRATIONS

In the drawings, which illustrate what is currently considered to be the best mode for carrying out the invention, FIG. 1 is a view in longitudinal cross section of an embodiment of the implantable structure having a single inlet port;

FIGS. 8–11 are charts illustrating the values of insulin delivery in four experimental sheep implanted with devices containing insulin;

FIGS. 12–15 are charts illustrating the effects of insulin boli given the four experimental sheep implanted with devices containing insulin.

DETAILED DESCRIPTION OF THE ILLUSTRATED EMBODIMENTS

Figure 1:
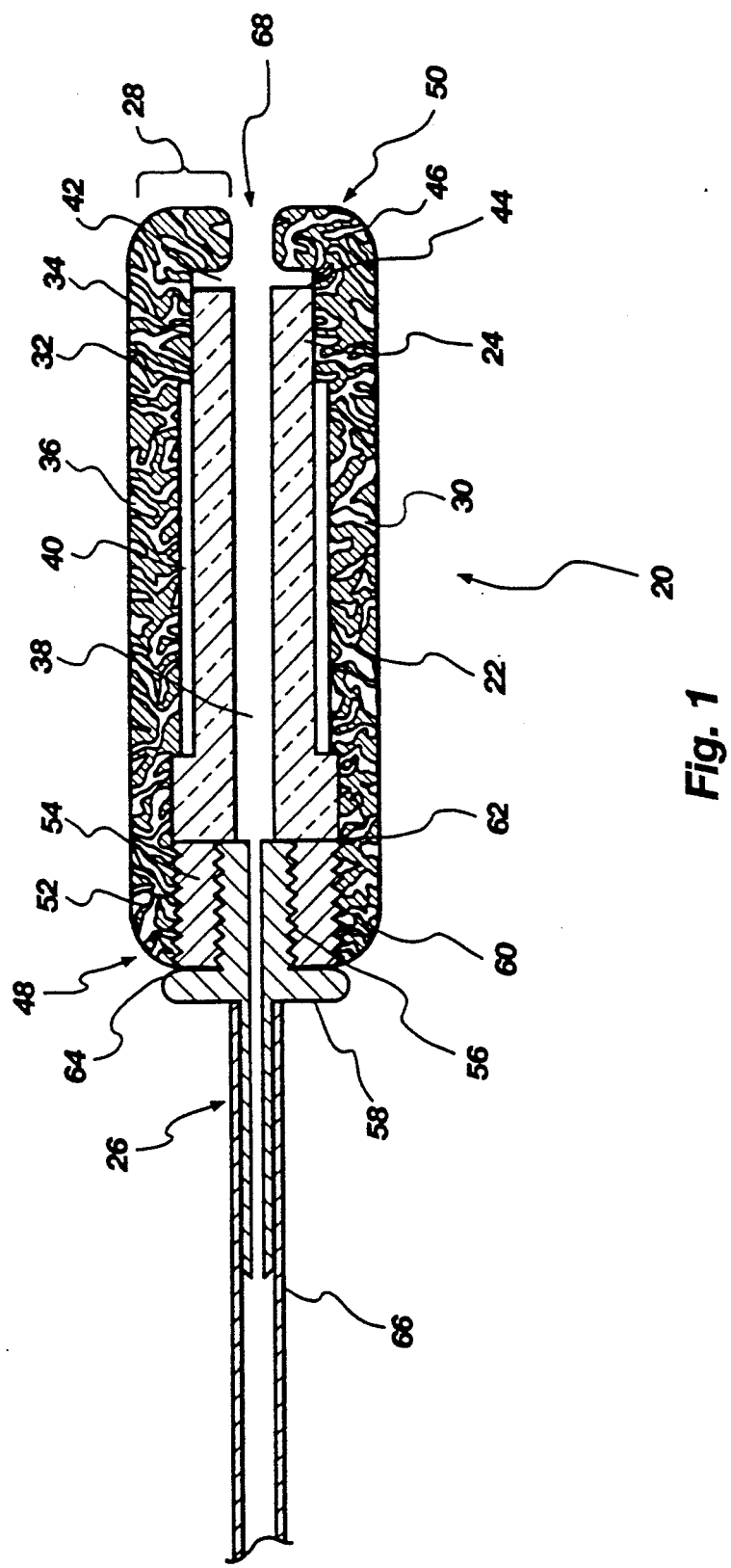
FIG. 1A is a view in longitudinal cross section of an embodiment of the implantable structure in which a glucose sensor has been placed.

The implantable structure 20 of the present invention generally comprises a porous outer member 22, a selectively permeable inner member 24 and at least one port means 26. The embodiment illustrated in FIG. 1 shows a simple configuration having a single port means 26. Hence, this embodiment may be termed a "flow through" device.

In this embodiment, the outer member 22 is constructed of a porous synthetic material having irregularly shaped and sized pores forming a tortuous pathway through the thickness 28 of the outer member 22. Some of the pores may be termed "open-celled" pores 30 since they form a continuous pathway from the exterior surface 32 of the outer member 22 to the interior surface 34 of the outer member 22. Some pores may be termed "close-celled" pores 36 since they have only a single opening associated with either the exterior surface 32 or interior surface 34 of the outer member 22. The pores, both open-celled and close-celled, may interconnect to form communicating pathways therebetween.

A particularly suitable material usable for forming the outer member 22 is Medpor ® (Porex, Inc., Fairburn, Ga.). Medpor ® is a high density polyethylene material having an intricate network of omnidirectional pores with irregular conformation. Any type of porous synthetic material may be used which is non-antigenic and inert in the body. For the purposes of this invention, "synthetic" means any material which is manufactured and not naturally occurring; "synthetic" materials may therefore include inert metals, polymers of rubber or plastic, and naturally occurring materials, such as collagen, which may be manufactured and/or treated for use in the invention. Polyethylene is a particularly suitable synthetic material for use in this invention because of its inert properties.

The pores of the outer member 22 are sized to allow ingrowth of vascularized connective tissue therethrough from the surrounding environment in which the implantable structure 20 is surgically placed. Pore size, for the purposes of this invention, may range from about 60 to about 500 microns, and preferably may be from about 160 microns to about 300 microns.

The outer member 22 may take any geometrical or other form which is suitable for surgical implantation.

As illustrated in FIG. 1, the outer member may be tubular in shape. The inner member 24 is positioned within the outer member 22. The inner member 24 is formed of a selectively permeable material which allows molecules of a certain size to pass therethrough, but will not allow growth of tissue therethrough. A pore size of up to 25 microns is particularly suitable in this embodiment. However, any synthetic material may be used which has the capability of allowing molecules with a molecular weight of 30,000 to about 100,000 Daltons or less to pass therethrough. A particularly suitable material is polysulfone.

The inner member 24 is shown in FIG. 1 as a tube which fits within the outer member 22. An inner space 38 is formed by the inner member 24. A space 40 is provided between the inner member 24 and the outer member 22 around the periphery of the inner member 24, and a space 42 is provided between the end 44 of the inner member 24 and the end 46 of the outer member 22. The spaces 40, 42 provide an area for growth of soft, highly vascularized tissue which enhances absorption of fluids by the tissue.

Both ends 48, 50 of the outer member 22 and inner member 24 are open. The first end 52 of the outer member 22 is configured to provide means for attachment of an inner collar 54 thereto. As shown in FIG. 1, the outer member 22 is formed with threads 56 which engage reciprocating threads of the inner collar 54. Port means 58 are secured to the inner collar 54, such as by threaded means 60. A silicone seal 62 may be positioned between the inner member 24 and the inner collar 54, and a silicone seal 64 may be formed between the inner collar 54 and the port means 58 for preventing leakage. The port means 58 is configured to provide communication of substances to the inner space 38 of the structure 20. A conduit 66 is secured to the port means 58 and provides a pathway for substances from a pump (not shown) or subcutaneously implanted injection port (not shown) to the port means 58. The use of pumps and injection ports are well-known in the art and are particularly described in U.S. Patent No. 5,100,392, referenced hereinabove.

The configuration of the implantable structure 20 in FIG. 1 is illustrative of one means of constructing the structure 20 without using adhesives. Because many suitable materials for manufacturing the structure, such as polyethylene, are not readily bondable by adhesive means, a manner of constructing the device without use of adhesives is particularly suitable. However, non-toxic adhesives may be used to join the various parts of the structure where appropriate. When used with porous material of the type forming the outer member, adhesives provide an advantageous mechanical bond due to the adhesive filling the pores.

In the flow-through embodiment shown in FIG. 1, the second end 50 of the outer member 22 and inner member 24 are open. When implanted in the body, vascularized tissue grows into the pores of the outer member 22 but stops at the inner member 24, the pores of which are too small to allow ingrowth of tissue. Vascularized tissue may also grow over the open end 68 of the structure 20, and the inner space becomes effectively a closed space into which material may be introduced. Tissue may grow into the open end 68 of the structure but will not occlude the device because fluid flowing into the inner space 38 effectively keeps tissue ingrowth to a minimum. After the structure 20 has been implanted in the body and tissue has grown into the outer member 22 and over the open end 68, fluid materials may be introduced into the inner space 38 via the port means 26.

Figure 1A:
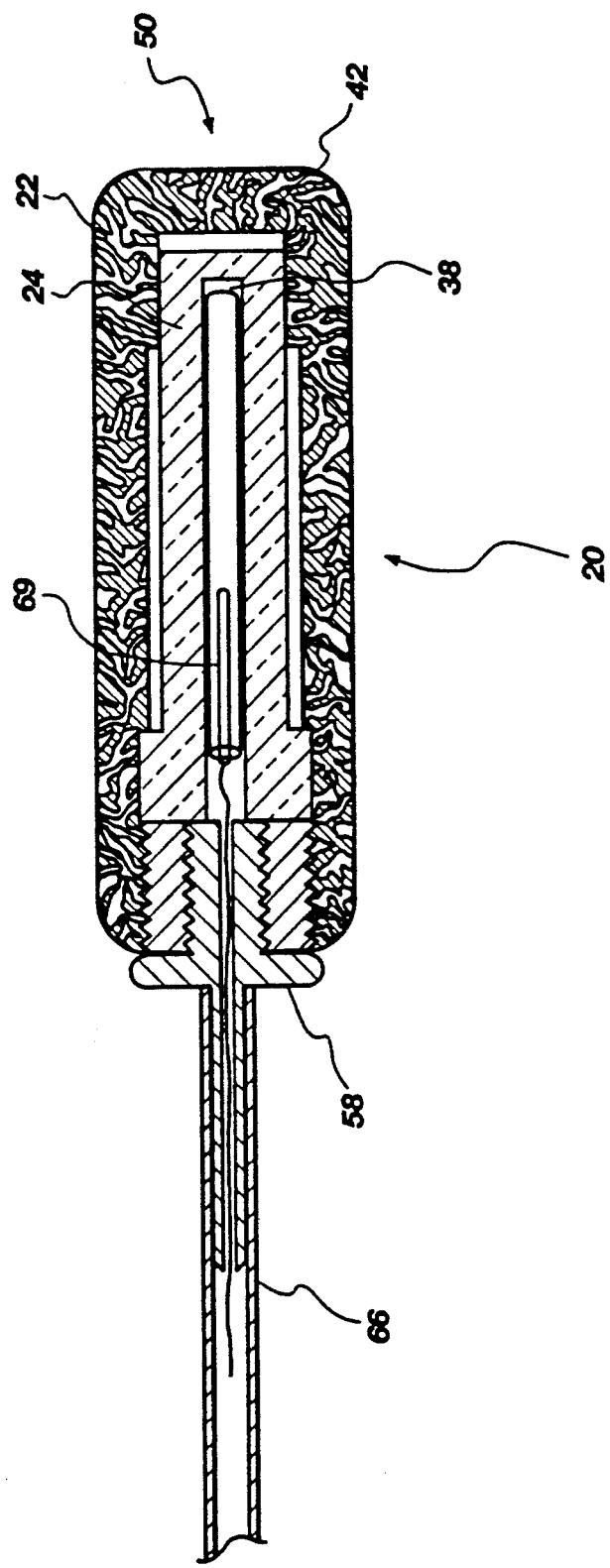

The implantable structure 20 may be used to house a glucose sensor 69, as shown in FIG. 1A. Implantable glucose sensors have been developed to evaluate glucose levels in the body and to signal an insulin pump to release insulin accordingly. A representative glucose sensor is described in Clark, et al. "Long-term Stability of Electro-enzymatic Glucose Sensors Implanted in Mice," *Trans. Am. Soc, Artificial Internal Organs*, Vol. 34, pp. 259-265 (1988). Glucose sensors have limited lifespans, however, and must be rejuvenated or replaced. Thus, the present invention provides a means for introducing a glucose sensor into a permanently incorporated housing and provides means for removing or replacing the glucose sensor over time. When placed in a closed-end device (a device where the end 50 of the device is not open) as shown in FIG. 1A, chemicals associated with the glucose sensor which become depleted over time can simply be injected into the innerspace 38 to rejuvenate the sensor. The small pore size of the inner member 24 prevents protein accumulation of the glucose sensor, which would adversely affect its operation.

Figure 2:
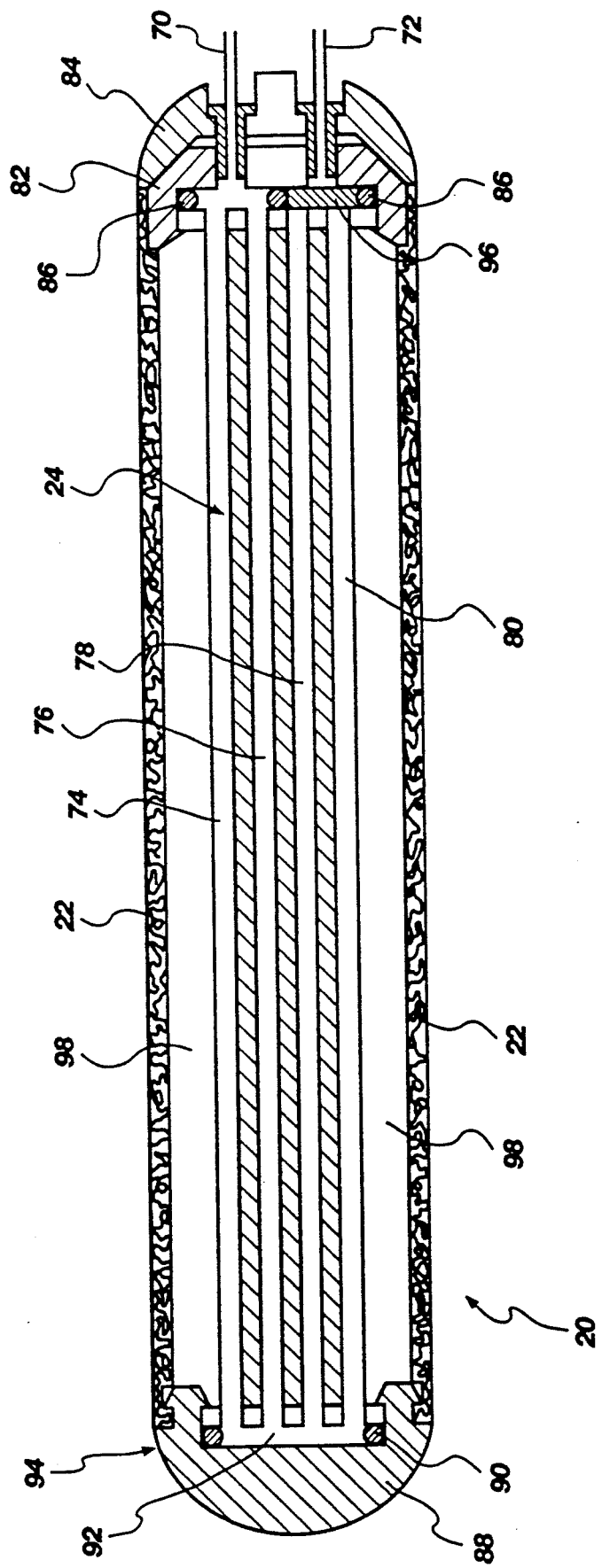
FIG. 2 is a view in longitudinal cross section of an embodiment of the implantable structure having an inlet port and an outlet port.

In an alternative embodiment shown in FIG. 2, the implantable structure 20 is configured with an inlet port 70 and an outlet port 72, thereby providing a closed-loop circulation pathway for injected substances. The outer member 22, shown in FIG. 2 as a tube, is made of porous synthetic material having irregularly shaped pores, as described previous. The pore size of the outer member may be from about 160-300 microns. The inner member 24 is comprised of a plurality of tubules 74, 76, 78, 80 constructed from a selectively permeable synthetic material, such as polysulfone with a molecular weight cut off of about 30,000 to 100,000 daltons (Amicon Div. W.R. Grace & Co., Beverly, Mass.).

One end of the tubules 74, 76, 78, 80 are positioned within a manifold housing 82 which is, in turn, positioned within a proximal end cap 84. A gasket 86 is positioned within the manifold housing 82 to prevent leakage of fluid therethrough. The other end of the tubules 74, 76, 78, 80 are positioned in a distal end cap 88, and a gasket 90 is positioned with the distal end cap 88 to prevent leakage of fluid therethrough. The proximal end cap 84, distal end cap 90 and manifold housing 82 are machined of high density polyethylene and are designed to snap together to avoid problems in bonding the materials. The gaskets 86, 90 may preferably be molded silicone rubber. The poly-sulfone tubules may be joined to the end caps using epoxy-(FDA-2LV, Tra-Con, Inc., Medford, Mass.) filled wells formed in the polyethylene.

Aligned apertures are formed through the manifold housing 82 and the proximal end cap 84 to provide placement of an inlet port means 70 and placement of an outlet port means 72 therethrough. The inlet and outlet port means provide access to the inner polysulfone tubules 74, 76, 78, 80. To form a continuous channel, all of the tubules 74, 76, 78, 80 terminate in a common chamber 92 at the distal end 94 of the implantable structure 20. Some of the tubules 74, 76 are aligned with the inlet port means 70 to receive fluid substances injected into the tubules 74, 76 via the inlet port means 70. The fluid substances travel to the common chamber 92 of the structure and from there enter into other tubules 78, 80 which are associated with the outlet port means 72.

A filter 96 is positioned between the tubules 78, 80 leading to the outlet port means 72 and the outlet port means 72. The filter has a pore size of about 80 to about 100 microns. The filter 96 serves to dilute substances, Such as islet cells, when the system is being filled.

Following implantation in the body, vascularized tissue grows through the outer member 22 and fills the space 98 formed between the outer member 22 and the tubules 74, 76, 78, 80. Ingrown tissue surrounds the tubules 74, 76, 78, 80 but cannot enter through the walls of the tubules. A fluid substance, such as insulin or islet cells in a liquid solution, is injected through the inlet port 70 by a conduit (not shown) interconnected between the inlet port 70 and a pump (not shown) or a subcutaneously placed injection port (not shown). In the case of instillation of islet cells into the system, for example, glucose from the well-vascularized ingrown tissue travels through the walls of the tubules 74, 76, 78, 80 and signals the islet cells to produce insulin. Insulin then exits through the walls of the tubules 74, 76, 78, 80 and is diffused into the surrounding vascularized ingrown tissue. When the islet cells have aged or become ineffective, the islet cells may be suctioned or flushed out through the outlet port means 72, and new islet cells may be introduced through the inlet port means 70.

Figure 3:
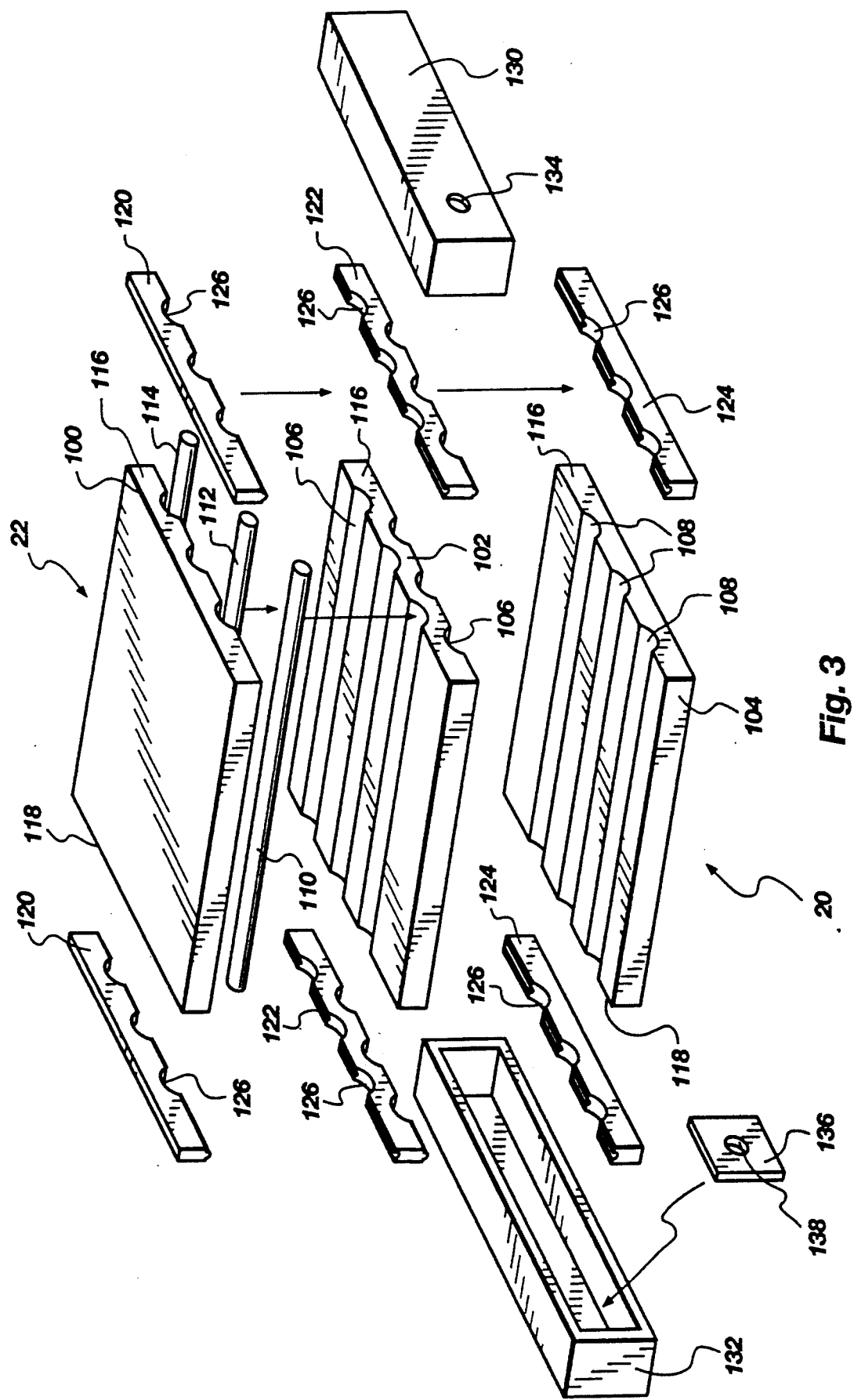
FIG. 3 is an exploded view in perspective of an alternative embodiment of the implantable structure.

FIG. 3 illustrates an alternative embodiment of the implantable structure 20 where the outer member 22 is comprised of a plurality of individual sheets 100, 102, 104 of porous synthetic material having irregularly shaped pores, as described previously. The individual sheets 100, 102, 104 of porous synthetic material are formed with elongated grooves 106, 108 into which individual tubules are positionable when the sheets are stacked. Although only a few tubules 110, 112, 114 are illustrated in FIG. 3, a tubule is positioned in every groove provided.

The ends of the tubules extend beyond the edges 116, 118 of the individual sheets 100, 102, 104 when the sheets are stacked together. End plates 120, 122, 124 are formed with notches 126 therein and cradle the ends of the tubules 110, 112, 114. When the individual sheets 100, 102, 104, the tubules 110, 112, 114 and end plates 120, 122, 124 are stacked together, a proximal end cap 130 and a distal end cap 132 fit over the ends of the stack. The proximal end cap 130 has an aperture 134 formed therein for communication of fluids into the structure 20. As may best be seen in FIG. 4, the distal end cap 132 is slightly wider than the stack formed from the outer member, the inner tubules and the end plates. Therefore, a space is provided for placement of a conduit cap 136 for communication of fluids out of the structure 20.

Figure 4:
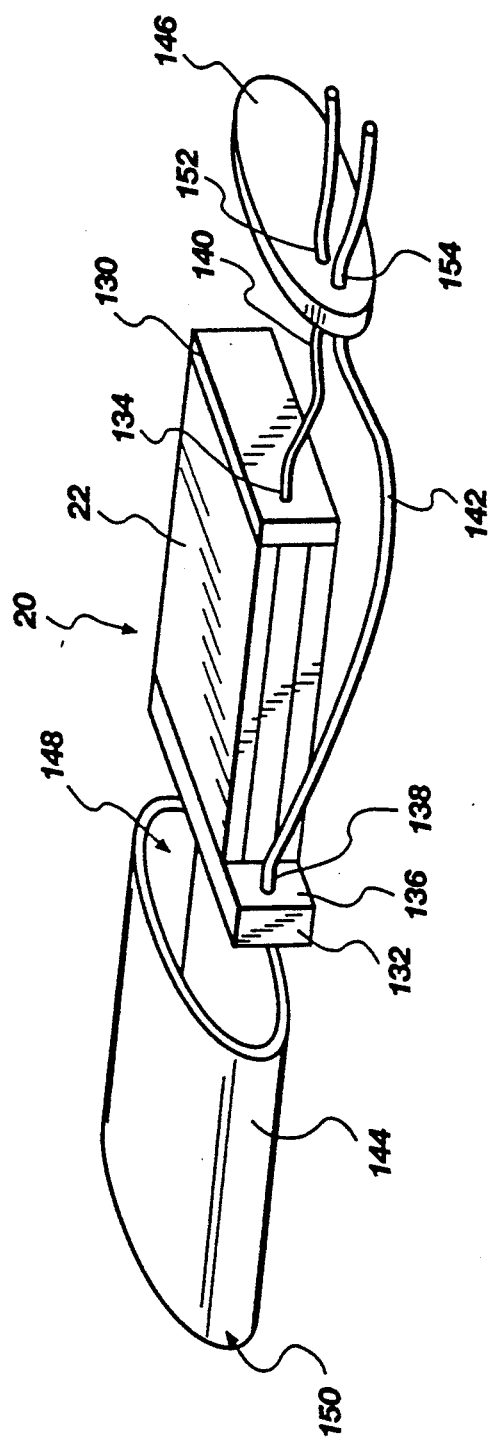
FIG. 4 is a view in perspective of the implantable structure shown in FIG. 3 when assembled.

The stacked structure 20 is illustrated by FIG. 4 where it may be more readily seen that an inlet conduit 140 is associated with the aperture 134 formed in the proximal end cap 130, and an outlet conduit 142 is associated with the aperture 138 formed in the distal end cap 132. The stacked structure 20 may be placed within a porous outer housing 144 sized to receive the stacked structure 20, and a cover plate 146 may be secured to the end 148 of the outer housing 144 to retain the stacked structure 20 therein. The other end 150 of the outer housing 144 is closed. The cover plate 146 has an inlet aperture 152 formed therein through which the inlet conduit 140 is positioned, and an outlet aperture 154 through with the outlet conduit 142 is positioned.

The outer housing 144 is constructed of coarsely porous synthetic material, such as polyethylene. The outer housing 144 may have irregularly shaped pores, as described previously, or more regularly shaped pores. The outer member 22, as described previously, is constructed of porous synthetic material having irregularly shaped pores, with a pore size of about 160-300 microns. Therefore, following implantation, vascularized tissue grows through the wall of the outer housing 144 and into the outer member 22 comprised of individual sheets 100, 102, 104 of material. The tissue grows only to the outer surface of the tubules 110, 112, 114 where it stops. The end plates 120, 122, 124, which may be made of substantially non-porous material, prevent tissue from growing into the proximal end cap 130 and the distal end cap 132.

Fluid substance, such as insulin or islet cells in a liquid medium, is introduced through the inlet conduit 140 and into the proximal end cap 130. The fluid substance travels into the tubules 110, 112, 114 and fills the distal end cap 132. When it becomes necessary to supplement or replace the fluid substance inside the tubules, the substance is suctioned or flushed through the outlet conduit 142, and new fluid substance is introduced into the tubules via the inlet conduit 140. The inlet conduit 140 is attached to a pump (not shown) or a subcutaneously placed injection port (not shown), either of which can be used to supply fluid substances to the structure 20.

The configuration of FIGS. 3 and 4 provides some self-locking construction. However, the proximal end cap 130 and the distal end cap 132 may be secured to the ends of the stack by a suitable adhesive, such as epoxy (FDA-2LV, Tra-Con, Inc., Medford, Mass.). In addition, the cover plate 146 may be secured to the outer housing 144 by a suitable adhesive.

Figure 6:
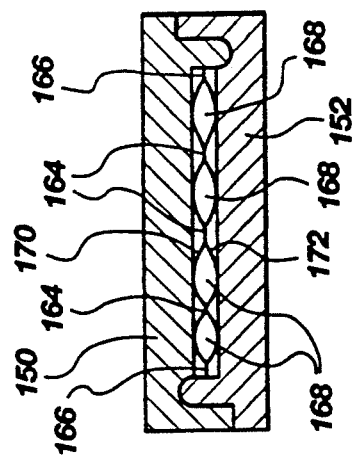
FIG. 6 is a view in lateral cross section of the implantable structure shown in FIG. 5 taken at line 5—5.
Figure 5:
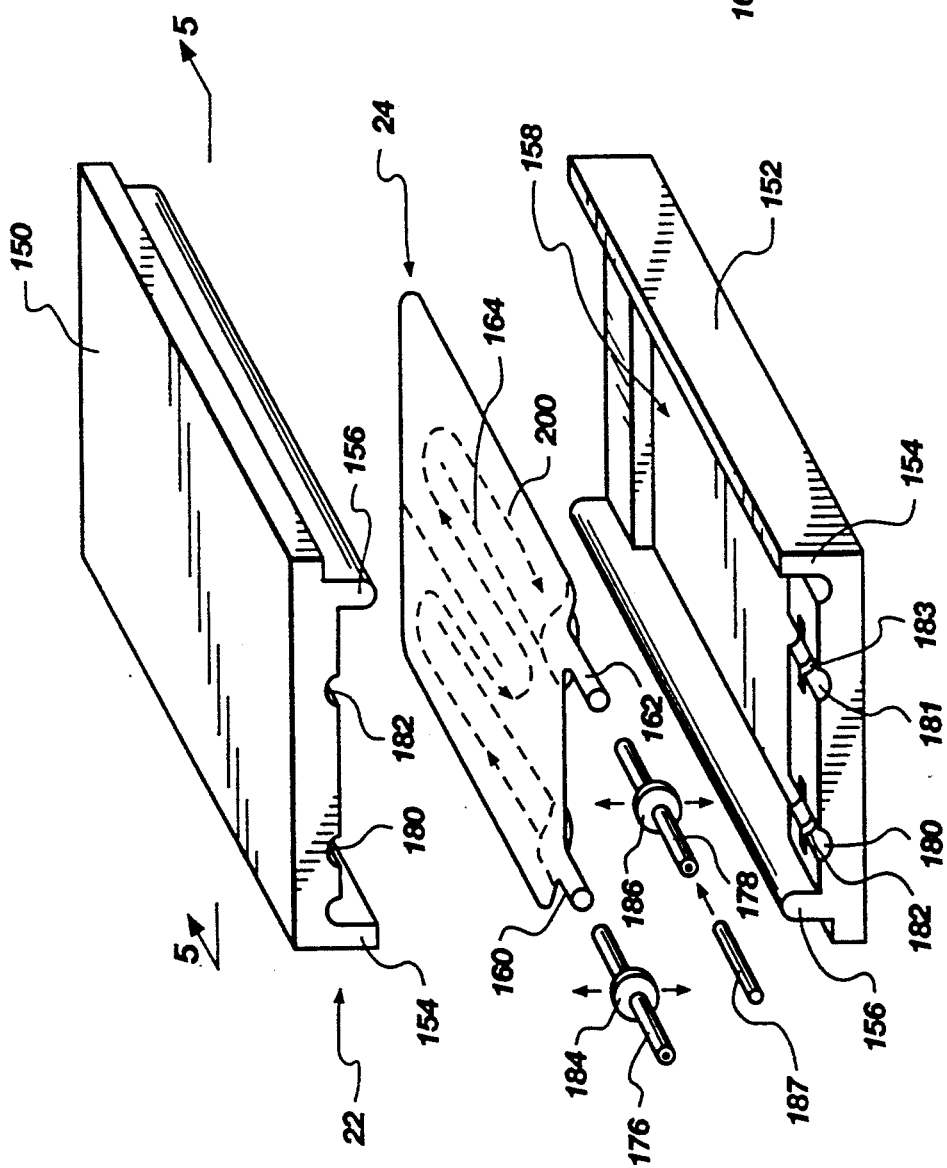
FIG. 5 is an exploded view in perspective of an alternative embodiment of the implantable structure.

The alternative embodiment shown in FIGS. 5 and 6 provides an interlocking construction with which adhesives may be used, but need not be used as noted previously. The outer member 22 comprises a first plate 150 and a second plate 152, each have interlocking flanges 154, 156 which provide a snap fit of the first plate 150 and second plate 152 together. As described previously, the first and second plates 150, 152 of the outer member 22 are formed of porous synthetic material having irregularly shaped pores. The pore size of the outer member 22 may be about 160-300 microns.

When the first plate 150 and second plate 152 are conjoined, a bed 158 is formed therebetween which is sized to receive and retain the inner member 24 therein. The inner member 24 is constructed from two sheets of selectively permeable material, such as polysulfone, which are heat sealed together around the periphery thereof except for two connector nipples 160, 162 which remain open. The two sheets of synthetic material are also heat sealed in the center, as indicated at the dotted lines 164, to form a winding pathway between the two sheets. The formation of the heat seals along the periphery 166 of the two sheets and in the center of the sheets, at 164, may be better seen in FIG. 6. Thus, spaces 168 are formed between the upper sheet 170 and the lower sheet 172 through which fluid substances may circulate.

An inlet tube 176 is secured to a first connector nipple 160 of the inner member 24. An outlet tube 178 is secured to a second connector nipple 162 of the inner member 24. The first plate 150 and second plate 152 have aligned notches 180, 181 to accommodate the inlet tube 176 and the outlet tube 178, respectively. The notches are further configured with insets 182, 183 to accommodate collars 184, 186 associated with the inlet tube 176 and outlet tube 176, respectively. A filter 187 having a pore size of about 25 to about 100 microns may be positioned within the outlet tube 78 to filter cells or substances from solution during flushing and replacement procedures.

As described previously, vascularized tissue from the surrounding environment where the structure is implanted grows into the pores formed in the first plate 150 and second plate 152. The tissue fills those areas of the bed 158 which are not occupied by the inner member 24. Fluid substances are introduced into the inner member 24 via the inlet tube 176 which is connected to a pump (not shown) or a subcutaneously implanted injection port (not shown). The fluid substance circulates through the pathway formed between the two sheets 170, 172 of heat sealed material forming the inner member 24, as indicated by the arrows at 200. New or supplemental fluid can be introduced into the inner member 24 by flushing or suctioning out the old fluid through the outlet tube 178.

The embodiments previously described may be used for introduction of medicinal substances, such as insulin, hormones, analgesics and the like, into the body. The embodiments described may also be used to introduce cellular or tissue material into the implantable structure to produce artificial endocrine organs. The implantable structure may further be used to implant viruses or oncological cell cultures into the body to evaluate drug therapies. Examples of instillation of islet cells and instillation of insulin follow:

EXAMPLE I

Evaluation of the physiologic response of islets contained in the implantable structure were performed in vivo by placing a dual port implantable structure (as shown by FIG. 2) into the abdominal cavity of a dog weighing approximately 20 Kg. The dog was pre-operatively prepared and anesthetized according to IACUC protocols. The dog was placed in right lateral recumbency on the surgical table. A left flank incision was made and the abdomen entered. A subcutaneous pocket was created cranial and caudal to the incision and an injection port was placed in each pocket. Connecting catheters were interconnected between each injection port and the inlet and outlet apertures of the device. The device was wrapped with the omentum of the dog and the omentum was secured with 3/0 Vicryl sutures. The omentum was attached to the body wall with 3/0 Vicryl sutures to prevent visceral torsion, and the incision was then closed. Postoperative treatment followed IACUC protocols.

Three weeks elapsed to allow incorporation of the device into the surrounding tissue by means of ingrowth of vascularized tissue into the device. The dog was pancreatectomized two months after implantation. Pancreatectomy was accomplished by mobilizing the pancreatic blood supply while preserving the recurrent duodenal branch of the gastroduodenal vessels and branches of the superior mesenteric vessels to avoid duodenal necrosis. The main pancreatic duct was ligated at its entrance to the duodenum, and the ducts to the right and left pancreatic limbs were cannulated separately with 20-gauge stub adaptors. The blood vessels to the mobilized pancreas were divided between clamps, and the fresh pancreas was placed in cold RPMI media 1640 solution (Gibco-brl Catalog #380-2400 (1990) Grand Islands, N.Y.).

Islets from the pancreas of the dog were isolated according to Hess, et al., "Comparison of Two Methods of Islet Preparation and Transplantation in Dogs," *Diabetes*, vol. 35, pp. 1109–118 (1986). The cannulated canine pancreas was intraductally infused (flow 25 ml/min., pressure 50 cm $H_2O$) with 150–200 ml of collagenase (Sigma Type I). Concentration of the collagenase was 7200 U/ml in Hanks' balanced salt solution, having a pH of 7.4, and infusion continued at room temperature for approximately four to eight minutes. Recirculation was performed using a roller pump. The distended pancreas was incubated and held stationary in 60 ml of collagenase solution at 37° C. for 20 minutes. After incubation, the collagenase-digested pancreatic tissue was bathed in RPMI media containing 10% newborn bovine serum (v/v), ampicillin, and gentamicin. The pancreatic tissue was gently stripped from the ducts with forceps, and the ducts and large vascular structures were discarded. The dispersed pancreatic tissue was triturated by a single aspiration and gentle flush through a 60 ml syringe without needle, and filtered through a steel mesh of 400 $\mu$m pore size. Tissue not passing through the screen was resuspended in RPMI media, agitated in a 4° C. shaking water bath for 10 minutes, and refiltered. The filtrate was centrifuged at 200×g for 60 seconds and was washed twice in RPMI.

Purification of islets from the dispersed pancreas were determined according to Hess, et al. About 30–40 milliliters of pancreatic tissue were recovered and were divided over 50 ml conical tubes in 3 ml aliquots and suspended in 12 ml of dextran. Another 4 ml of dextran were positioned beneath the tissue and the islet suspension was overlaid with 4 ml each of dextran having densities of 1.085, 1.075 and 1.041 respectively. The discontinuous gradient was centrifuged initially at 40×g for 4 minutes, then at 500×g for 12 minutes at 5°–10° C. The purified islet tissue was harvested from the uppermost two interfaces of the gradient, and was washed with cold RPMI media 1640 solution. The islets were suspended in 55 ml of RPMI.

Instillation of the autologous islet cells was performed immediately after their preparation. The dog was awake and in right lateral recumbency. No sedation was necessary, but could have been used if necessary. A 16 gauge Huber needle was placed in each of the caudal and cranial ports. The harvested islets were placed in 20 cc of RPMI media 1640 for injection. The solution containing the cells was injected into the device through the cranial port. Since the outlet pathway of the device contains a filter with a pore size of 1 to 25 microns, the fluid portion of the solution diffused through the filter and out the caudal needle. The filter thus prevented loss of the islets from the device. After all the cells were instilled the needles were removed.

Assessment of glucose metabolism was evaluated by determining initial baseline fasting peripheral plasma glucose and insulin (obtained from the cephalic vein) at the time the device was implanted, prior to pancreatectomy, and immediately prior to instillation of the autologous islets. Fasting blood glucose was followed once daily using a Glucoscan ™ (Lifescan, Inc., Mountain View, Calif.) glucometer. Insulin (RIA kit) determination was made as needed.

Exogenous insulin was administered to the dog as needed to maintain a blood glucose below 200 mg%. The initial cell instillation resulted in a blood glucose of 125 mg% with an insulin dose of 14 U/day. On day 15 the autologous cells were flushed out of the device and were replaced with xenogeneic islet cells of hamster origin. The hamster islet cells were HIT-T15 pancreatic beta insulinoma cells obtained from the American Type Culture Collection (Rockville, Md.). Cytologic examination demonstrated the removed autologous cells were viable.

Figure 7:
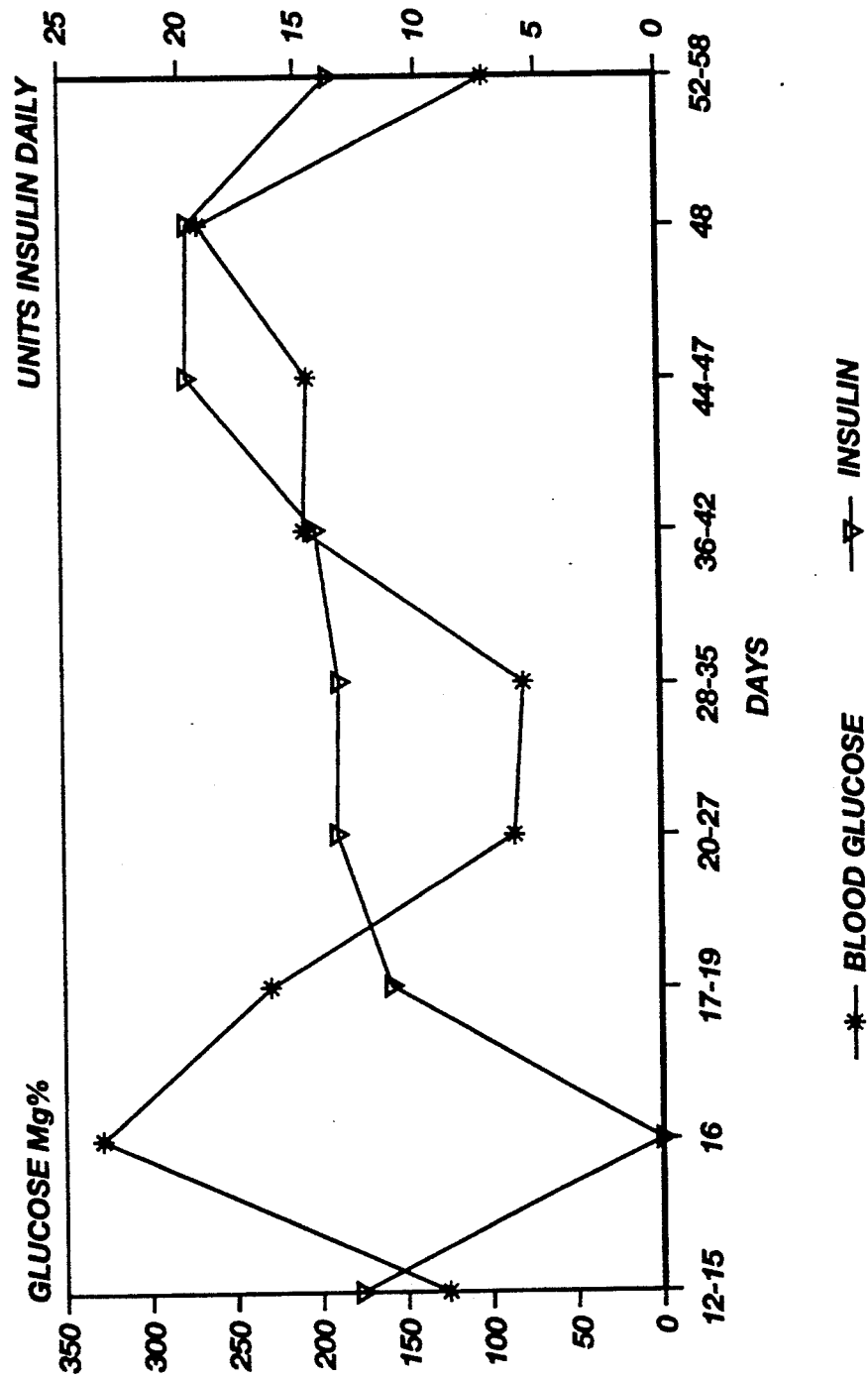
FIG. 7 is a graph illustrating relative levels of glucose and insulin in a dog implanted with a device containing islet cells.
Figure 16:
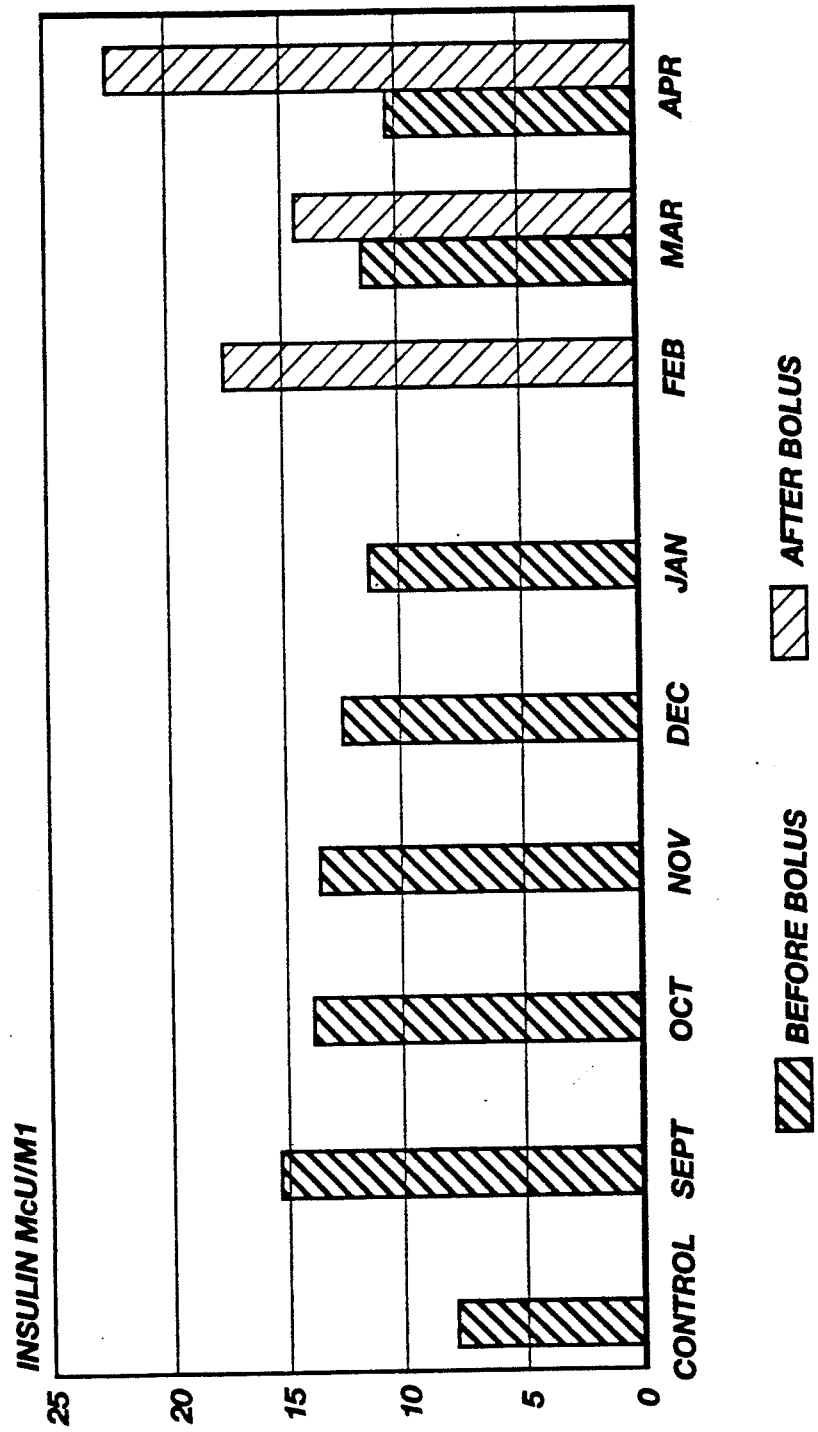
FIGS. 16–19 are bar graphs illustrating the average daily insulin levels existing in the four experimental sheep.
Figure 17:
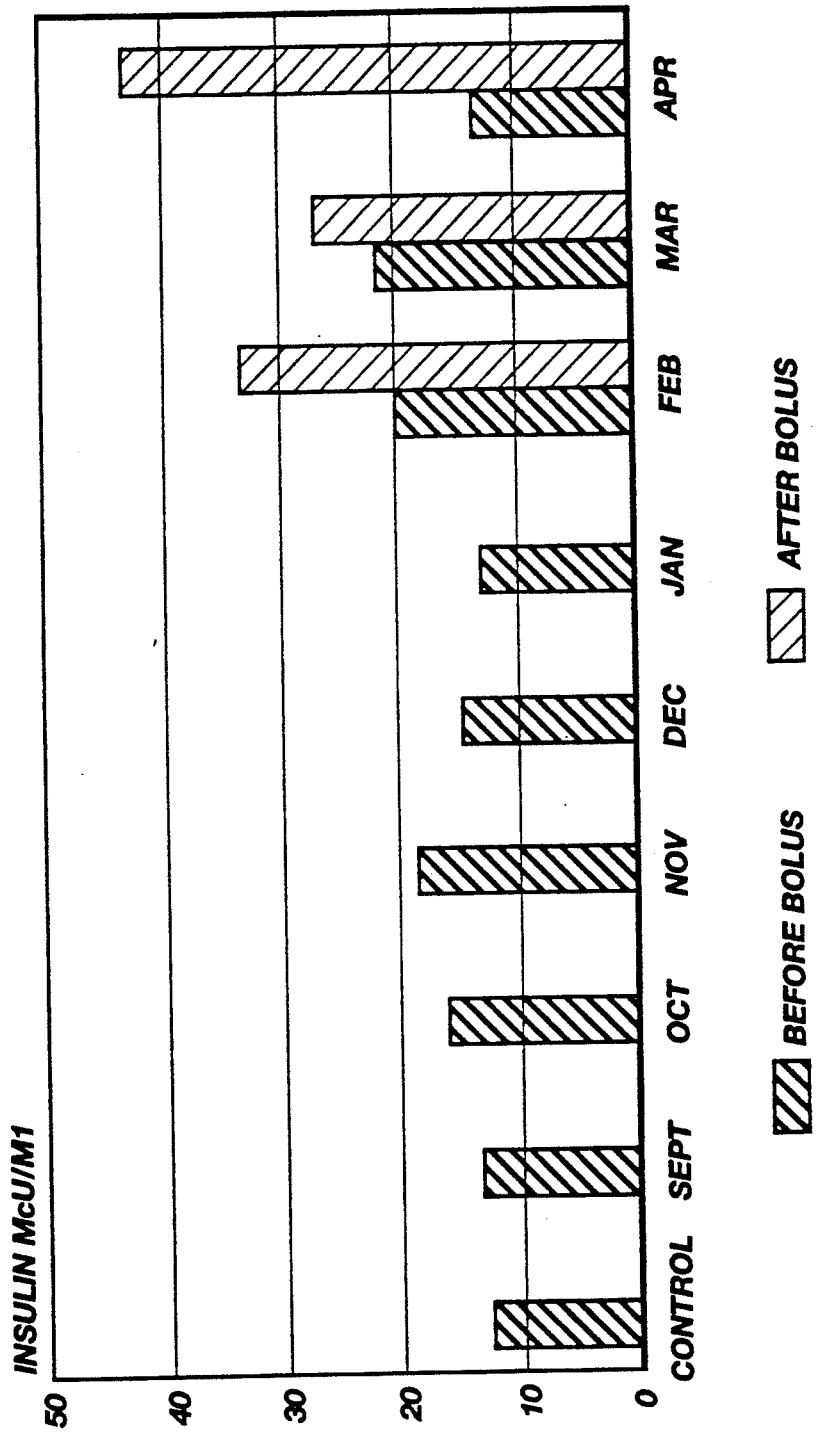
Figure 18:
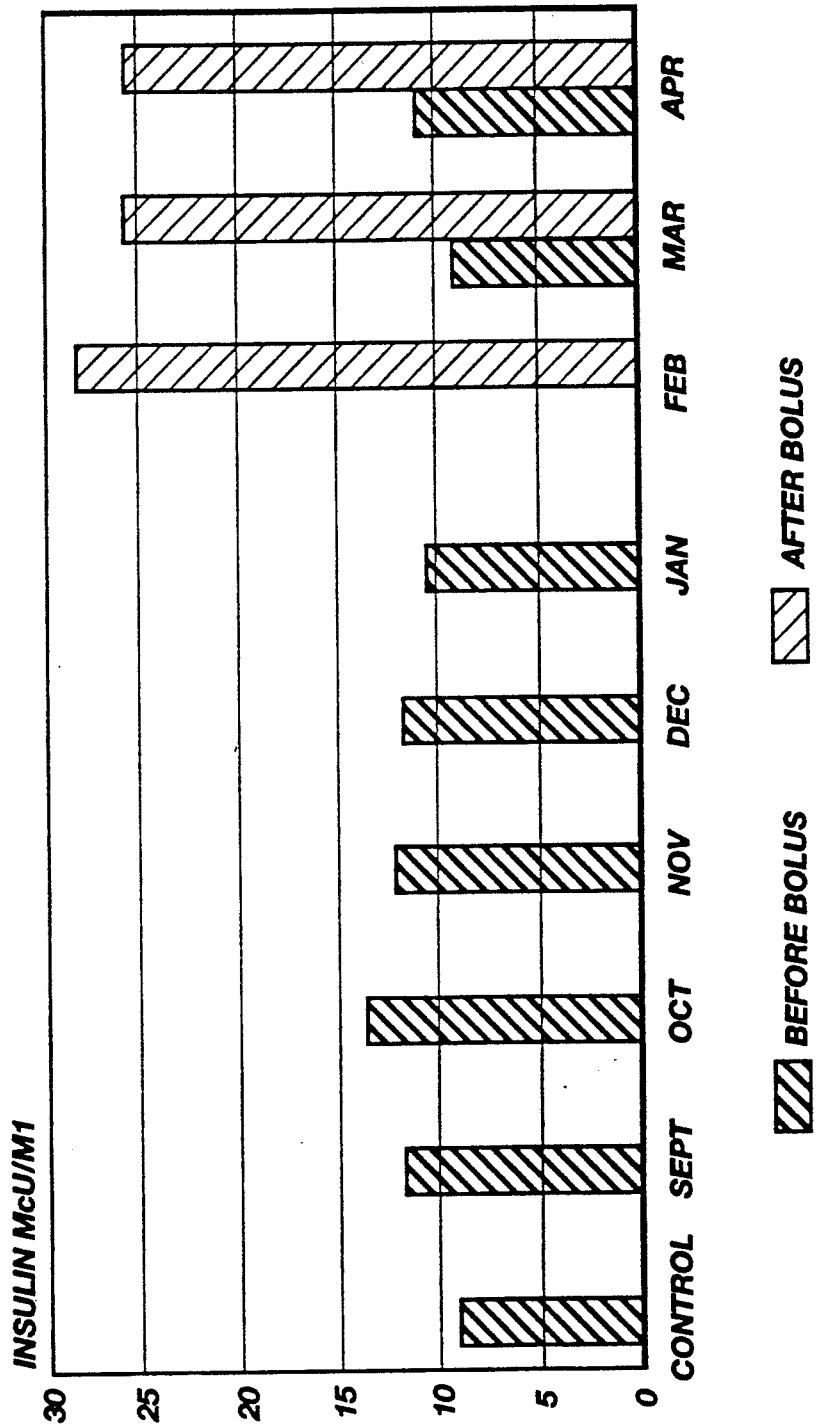
Figure 19:
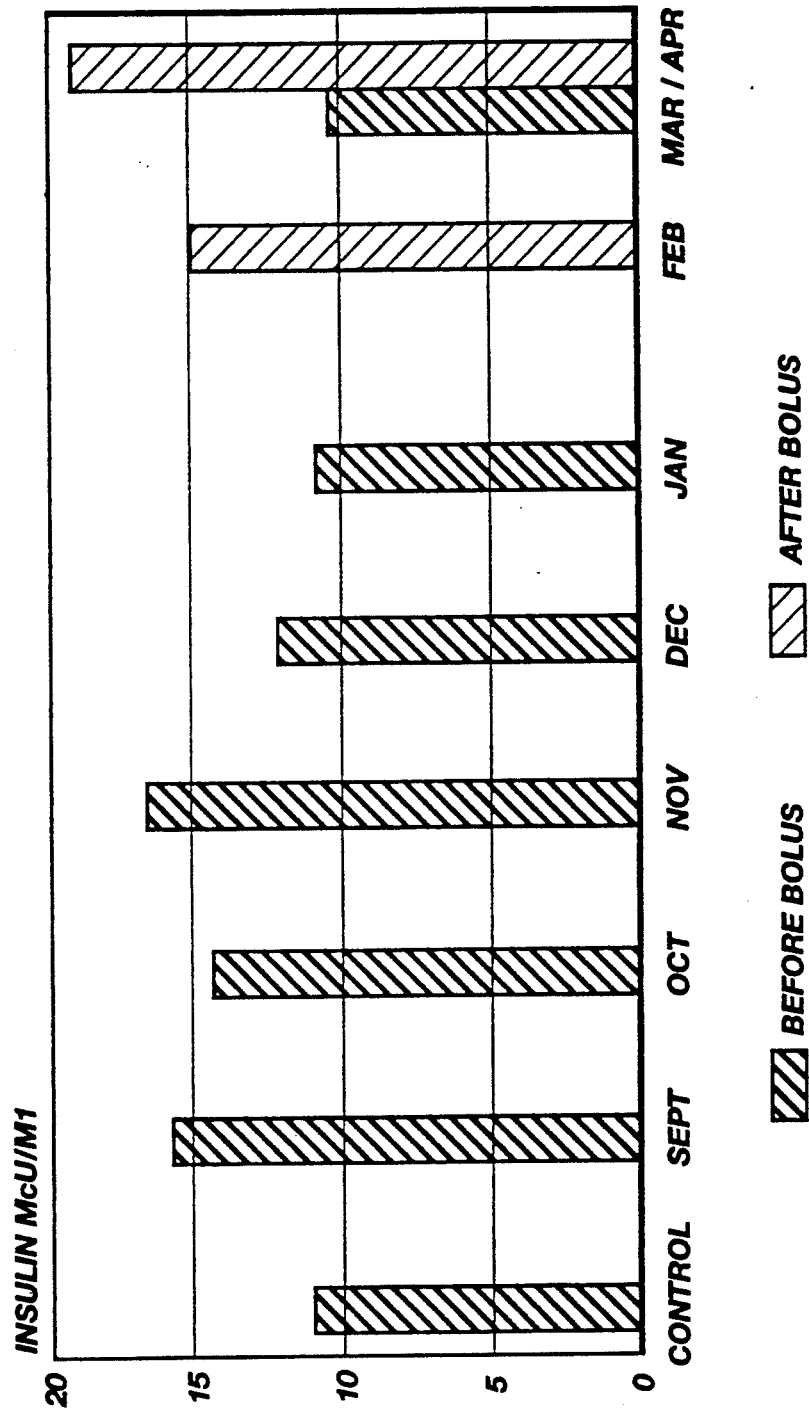

Referring to FIG. 7, insulin was not administered on days 15 or 16, resulting in a blood glucose of 340 mg %. Exogenous insulin was administered at a dose of 13–14 U/day on day 17. The blood glucose declined and by day 20 was 70 mg% at which level it remained. On day 35 the xenogeneic cells were flushed out. The blood glucose increased to over 200 mg% by day 36 with an insulin dose of 15 U/day. By day 47 the blood glucose was 260 mg % with an insulin dose of 22 U. On day 48 fresh xenogeneic hamster islet cells were placed in the device to supplement the previously instilled cells. The blood glucose fell to 70 mg % with an exogenous insulin dose of 14 U/day.

The results demonstrate indirectly that the hamster cell produced enough insulin to reduce the amount of exogenous insulin required to produce euglycemia.

The dog was sacrificed according to IACUC protocols. The caudal and cranial ports were exposed and the catheters traced back to the device. No evidence of adhesion, torsion, infection, or encapsulation was observed. The device and omentum were removed en block. The device was opened cross-sectionally and the tissue evaluated grossly. One half of the device was sectioned longitudinally. The cut section of the device was placed in formalin. Histologic slides were made of various sections of the device. The sections were evaluated for infection (bacteria), encapsulation, rejection (mononuclear cell infiltrate), and vascularity. The connective tissue appeared to be highly vascularized and viable.

The implantable structure can also be used to provide the delivery of a drug or other therapeutic substance to a patient. Use of the device to provide insulin is described hereinafter.

Example II

Four mature, 150–175 lb, non-diabetic sheep were utilized. Control blood insulin and blood glucose values were established for each sheep prior to implantation of the devices and pumps. Sheep #1 and #3 were implanted with a "flow through" device. A right flank incision was made through the skin. A 10 cm subcutaneous pocket was created cranial to the incision for implantation of a pump. The abdominal muscles of the sheep were separated and the peritoneum incised. A segment of omentum was exteriorized. An insulin pump was placed in the cranial pocket. The proximal end of a connecting catheter was attached to the pump, and the distal end was passed into the abdomen. The distal end of the pump catheter was attached to the inlet port means of the device.

The device was wrapped with omentum and the omentum fixed to itself. The device was placed within the abdomen. The interconnecting catheter was examined for kinks. The abdomen was closed. The pump was fixed within the subcutaneous pocket and the skin was closed. The pump was filled prior to implantation.

Sheep #2 and #4 were implanted with a dual port device (as shown in FIG. 2). A right flank incision was made through the skin. A 10 cm subcutaneous pocket was created cranial to the incision for implantation of a pump. A 2 cm subcutaneous pocket was created caudal to the incision for implantation of an injection port. The abdominal muscles were separated and the peritoneum incised. A segment of omentum was exteriorized. The pump was placed in the cranial pocket and the port in the caudal pocket. The proximal end of the connecting catheter was attached to the pump, and the distal end passed into the abdomen. A silastic button was fixed to the muscle fascia cranial to the incision. The distal end of the pump catheter was attached to the inlet port of the device. The proximal end of the injection port connecting catheter was attached to the injection port. The distal end was passed through the abdominal muscles, caudal to the incision, and was attached to the outlet port of the device.

The device was wrapped with omentum and the omentum was fixed to itself. The device was placed within the abdomen. The connecting catheters were examined for kinks. The abdomen was closed. The pump and injection port were fixed within the subcutaneous pocket and the skin was closed. The pumps and ports were filled prior to implantation.

Glucose Evaluation

Blood glucose was evaluated daily using a Glucoscan glucometer for measurement. The time of day for sampling was varied.

Blood Insulin Evaluation

Control insulin values were established prior to pump implantation. Insulin administration was begun 24 hours after pump implantation in Sheep 1P and 2P, and 3 weeks after implantation in Sheep 3P and 4P. Blood for insulin measurement was obtained from the external jugular vein twice weekly. Time of day of bleeding was varied.

The daily insulin dosage varied and, at about the fourth month of implantation, a daily bolus of insulin was administered in conjunction with the daily basal rate to evaluate the device's response to a single bolus of insulin. A single bolus mimics a pre-meal bolus. The insulin pump was programmed to deliver a specific amount of insulin over a 24 hour period. The single bolus was delivered in addition to that.

Pump Bolus Studies

A decision was made the third month after implantation to evaluate the peripheral blood insulin levels separate from pump diagnostic studies. This would allow evaluation of the insulin response from a single 100 µl pump bolus. Evaluation was made from the time of bolus initiation to the first appearance of insulin, the peak insulin value, and decay curve of the peripheral insulin values.

Pump Diagnostic studies

Pump diagnostic studies (PDP) were conducted in accordance with the techniques of Reich as disclosed in U.S. Pat. No. 5,006,997, the contents of which are incorporated herein by reference. The pressure wave forms produced by the insulin pump with the device were evaluated approximately every 30 days. Prior to PDP evaluation, the pump was emptied of insulin, and the amount of insulin was measured and recorded. The pump was then filled with fresh insulin and the amount recorded. The amount of insulin removed, and the amount replaced into the pump, were entered into the pump programmer. From this information the normalized flow rate was obtained. The peak pressure produced by the PDP bolus, the T time (time for pressure to return to ½ of peak), and the TDT time (time for the pressure to return to original baseline or to stop falling) were recorded. Usually, two PDP waves were run. The blood insulin and blood glucose values were followed during these studies.

The pressure wave form created by a 100 μl/12 minute pump bolus was also evaluated as to its slope over the 12 minute period. Experiments were conducted at the end of the study. The sheep were sacrificed, and the apparatus was evaluated as to function.

The devices were explanted and cut cross-sectionally into 5-6 pieces which were placed in 10% formalin. Slides were made from each section by straining with hematoxylin and eosin and they were examined by a Veterinary Pathologist.

Final insulin evaluations were conducted but these studies were flawed apparently because the sheep's body temperature fell to 36° C. or lower. The low temperature essentially shut down the portal circulation, and the result was reflected in the insulin values obtained. In addition, the sheep were anesthetized which also reduced portal blood flow.

Daily Glucose Evaluation

The control blood glucose values in the sheep ranged from 41 mg percent to 80 mg percent with the average for the four sheep of 57 mg percent. The daily glucose values after the sheep were implanted were within the same range. This normal value is lower than that of dogs or man and did not appear to be of value in evaluating function of the device.

Daily Blood Insulin Evaluation

The average control blood insulin values of the sheep were as follows:
1P 8 micro units/ml
2P 12.67 micro units/ml
3P 9.83 micro units/ml
4P 11.0 micro units/ml Column one of FIGS. 8, 9, 10 and 11 presents the average daily insulin delivery per day for each sheep programmed into the pump. Column two of each Figure presents the actual amount of insulin delivered to the sheep based on the pump normalized flow rate.

The average daily blood insulin is presented in column four of each of FIGS. 8, 9, 10 and 11. This value includes the daily single bolus insulin, but not the PDP or pump bolus studies. Column five presents the percentage of the delivered insulin seen in the peripheral blood. The values are an average of about one month's data and represent the days between each PDP study. An increase in the average daily insulin levels between the fifth and sixth month post implantation was observed reflecting the administration of a daily single 50 or 100 microliter bolus of insulin.

The percent of peripheral insulin dose varied, but not consistently. In Sheep #1 (FIG. 8) a low value in the sixth month was observed preceded by a value equal to the first month. A lower value in the eighth month preceded by a value equal to the second month is also shown. In Sheep #3 (FIG. 10) the eighth month value was higher than any of the preceding months. Sheep #4 (FIG. 11) showed a higher value in the eighth month than in the first or second months, the third month was higher than either.

In Sheep #2 (FIG. 9) the catheter separated from the implanted peritoneal device in the fifth month so that the insulin was being delivered through an open ended catheter. It is notable that in months six and seven the peripheral insulin values were only 0.07%, and only 0.10% in the eighth month.

FIGS. 16, 17, 18 and 19 also show the average daily insulin values over time and show the blood insulin values one to two hours after a 50 or 100 μl bolus was delivered as compared to insulin value obtained before a bolus. The daily insulin levels, not including the single bolus, show a bell curve shape, including Sheep #2 which had an open-ended peritoneal catheter. Also noted was the definite response to the single daily pump bolus injection in all the sheep. This suggests that the daily insulin levels for that time period, which approached the control levels, may have been a function of the liver and not absorption of the device. This is confirmed by the response seen in Sheep #2, having an open peritoneal catheter. This data also demonstrates that the response to a single daily bolus did not decrease over the last three months.

Pump Bolus Evaluation

FIGS. 12, 13, 14 and 15 present the data from the pump bolus studies, by days post implant. Note that the flow through devices (#1 and #3) showed the first appearance of insulin generally within 15 to 30 minutes of the initiation of the bolus, and a peak within 30 to 60 minutes of the bolus. Sheep #4, having a double lumen device, generally showed first appearance of insulin in 15 minutes, and it peaked at 15 to 30 minutes. However, the peak was never as high as peak experienced in the flow through devices unless a hand flush was done.

Sheep #2, with the disconnected double lumen catheter, showed a 15 minute first appearance with a 30 to 60 minute peak. This is similar to the flow through.

FIGS. 12, 13, 14 and 15 also show the fall off time from the peak insulin to return to baseline. The time to return to baseline was usually less in the flow through device than in the double lumen.

Sheep #3 underwent a double bolus study. The first appearance of insulin was at about 30 minutes, and represented the peak time also. At 2.5 hours there was a fall off of only 5.69 μU/ml. A second bolus was given at that time. The peak insulin was only 7.87 μU/ml over the original peak, and by two hours after the second pump bolus, had declined to 9.37 μU/ml.

A study was done where sheep #1 and #3 received three pump boli of 100 μ1 in the space of one hour. The peak values did not appear to be additive and the fall off time seemed to be the same as if only one bolus was given. Sheep #2, with three boli, showed the same type of curve, but the peak values were considerably higher, after the first bolus, resulting in a very low blood glucose.

Histopathologic Evaluation

Sheep #2 and #4 were implanted with double lumen devices which demonstrated a layer of dense fibrous connective tissue around them. Sheep #1 and #3 showed minimal to variable layers of dense fibrous connective tissue. In summary, there was more dense tissue around the double lumen devices than the flow through device.

All the devices demonstrated dense fibrous connective tissue within the lumen of the device. The connective tissue on the outer surface of the polyethylene was not the dense fibrous tissue of the lumen, but a looser connective tissue. As the tissue penetrated from the outside through the pores to the inside, it becomes more dense. This change was seen in all the devices.

The connective tissue growing through the pores was well vascularized. In fact, red blood cells and fibrin were identified in the hollow areas in the center of the devices. A lack of nuclei in some of the intraluminal connective tissue cells was observed.

It should be noted that insulin is a first pass drug. That is, the liver will remove 30 to 80 percent of the insulin on the first pass of insulin through the liver. Therefore, peripheral blood insulin values are not a direct reflection of the absorption of the drug from its injection site. This is obvious from the variability of the insulin data.

The stabilization effect noted for blood glucose was also seen with insulin. When the basal dose of insulin was increased, there was an initial increase in blood insulin levels, but they returned to basal levels.

As seen in FIGS. 16, 17, 18 and 19, the average daily insulin blood levels returned almost to the initial control levels by the eighth month after implantation. This occurred in Sheep #1 and #2 in which the amount of insulin that was delivered was higher during the last month than during the first month. The same occurred in Sheep #3 and #4, in which the amount of insulin delivered was less in the last month than in the first month. This pattern is seen in Sheep #2 even during the last two to three months, at which time the delivery site was essentially an open ended catheter delivering directly into the peritoneal cavity.

It is believed that these responses represent the effect of the liver on insulin metabolism. The liver appears to function in a manner to maintain a specific blood insulin level. It does this by removing insulin from the circulating blood. Since the liver removes 30% to 80% of the insulin on the first pass, it is able to regulate the peripheral blood insulin.

This concept of the liver increasing its ability to remove insulin is supported by the multiple insulin bolus studies. When multiple pump boll of 100 μU were administered over a one hour period, the peripheral insulin values were not linear. The rise between the last bolus and the first bolus were not as great as between the basal level and the first bolus.

It is possible to exceed the liver's ability to remove insulin by increasing the amount of insulin reaching it. This can be done by increasing the amount of insulin or by increasing the rate of absorption. When giving insulin directly into the peritoneal cavity, as was done in Sheep #2, the rate of absorption is increased since there is a greater surface area to absorb the insulin. This is demonstrated in FIG. 13 after the last pump bolus. This peak insulin value is contrastable with the lower values of Sheep #1, #3 and #4 (FIGS. 12, 14 and 15).

The device provides a specific tissue volume within its lumen. It also has a specific amount of blood flowing to it and away from it. When insulin is injected into the device it diffuses through the intraluminal extracellular tissue spaces until it reaches and enters the capillaries. Therefore, at a given interstitial/intraluminal pressure, the rate of absorption is set. The value in these studies appeared to be low enough that it does not overwhelm the liver's first pass ability. Even if an increased volume of drug is given, as was done in the multiple bolus studies, only a given amount of drug can diffuse into the portal circulation unless the intraluminal pressure is markedly increased. Markedly increasing the intraluminal pressure within the device, as was done by hand flushing, will result in a marked increase in the peripheral blood insulin. The increased pressure from the hand flush increases the interstitial diffusion rate allowing it to exceed the ability of the liver to remove it. Hand flushing is accomplished by inserting a needle into the pump side port or caudal port and injecting saline into the port with a syringe.

Most of the vascularity in the sheep occurred in the pores and outer tissues of the device. Therefore, the drug has to diffuse through a given volume of luminal tissue before being absorbed. It follows that if the luminal tissue volume were decreased, the rate of absorption would be more rapid. It appears that as the connective tissue within the device increases in density, the volume of interstitial space becomes less; therefore, the rate of transport is decreased. If the amount of insulin presented to the liver over a specific period of time is less, then the ability of the liver to remove insulin is not overwhelmed and a lower peripheral blood insulin is obtained.

The studies demonstrated that the device will deliver insulin to the peripheral circulation after seven months of implantation in sheep. Also, the studies demonstrated that insulin injected into the device will be reflected into the peripheral circulation of the sheep within 15 to 30 minutes after the start of a pump bolus. The same response time is seen in an open ended intraperitoneal catheter.

The present invention is directed to the implantation of a structure which is incorporable within the surrounding tissue, and which provides delivery of fluid substances to the body or to the implantation of tissues or cells which produce, or cause to be produced, biochemical substances needed by the body. Thus, the implantable structure of the invention has been described herein as being useful in the delivery of medicinal substances, such as insulin, and in the implantation of endocrine tissue, such as islet cells, in vivo. The implantable structure may also be used in vivo to perform prototype drug evaluation studies. For example, cells infected with certain viruses, such as HIV, may be instilled in an implanted device, and drug therapy may be administered to the animal to determine the efficacy of various prototype drugs on the virus. Further, cells from the implanted structure may be sampled from time to time to determine growth patterns in the cells. Hybridomas may also be instilled in an implanted structure to produce antibodies. The antibodies that are produced by the hybridomas may be removed from the inner space of the device for use in other contexts. Larger sized implantable structures implanted in a host animal would provide increased production amounts of antibodies thereby increasing the commercial availability of such substances.

The incorporable feature of the implanted structure has the potential for reducing the number of test animals that may be required in future research since the system may be flushed of cells or other biological substances and resupplied with other cells, tissues or substances. Thus, the same test animal may be used for a number of different cell or drug tests. The previously described evaluations, including testing of islet cells, may also be performed in vitro with the disclosed device.

The structure of the invention may be modified to meet the demands of the particular application. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims.

What is claimed is:

1. Implantable structure for incorporation into the body tissues of an animal to provide administration of substances from said implantable structure to said body tissues comprising:
    an outer member of porous synthetic material, the pores of said synthetic material being sized from about 60 microns to about 500 microns to provide ingrowth of vascularized connective tissue therethrough to effect incorporation of said implantable structure into said body tissues;
    an inner member of selectively permeable porous material positioned within said outer member and structured to provide immunoisolation to substances containable within said inner member, the pores of said selectively permeable material being sized to provide movement of macromolecules therethrough while preventing ingrowth of tissue therethrough and having a pore size of from about 30,000 Daltons to about 25 microns;
    an inner space formed within said inner member for placement of substances therein; and
    port means associated with said outer member and said inner member, said port means being in communication with said inner space to transport said substances to and from said inner space.

2. The implantable structure of claim 1 wherein said porous synthetic material of said outer member has irregularly shaped and sized pores defining a tortuous pathway through said material.

3. The implantable structure of claim 2 wherein said outer member has a first end and a second end, wherein said inner member has a first end and a second end, said first end and said second end of said outer member being aligned with said first end and said second end of said inner member, respectively, and said port means being secured in association with said first ends of said outer member and said inner member.

4. The implantable structure of claim 3 wherein said second ends of said of outer member and said inner member are closed.

5. The implantable structure of claim 4 further comprising glucose sensor means positionable within said inner space for evaluating extant glucose levels within said structure.

6. The implantable structure of claim 2 wherein said port means comprises an inlet port and an outlet port.

7. The implantable structure of claim 6 further including a filter positioned relative to said outlet port, said filter having a pore size of about 1 micron to about 25 microns.

8. The implantable structure of claim 7 wherein said inner member comprises a plurality of tubules configured to provide movement of said substances therebetween, said tubules being in fluid communication with said inlet port and said outlet port.

9. The implantable structure of claim 8 wherein said outer member comprises a plurality of sheets of porous synthetic material having spaces formed therein for positioning said tubules relative thereto.

10. The implantable structure of claim 9 further comprising an outer housing formed of porous synthetic material into which said outer member and said inner member are positionable, said pores of said outer housing being sized to provide ingrowth of vascularized connective tissue therethrough.

* * * * *